US009952207B2

(12) United States Patent
Iwamoto et al.

(10) Patent No.: US 9,952,207 B2
(45) Date of Patent: Apr. 24, 2018

(54) IMMUNOCHROMATOGRAPHY REAGENT COMPRISING A NONIONIC SURFACTANT, BICINE, AND CASEIN, AND MEASUREMENT METHOD USING THE SAME

(75) Inventors: Hisahiko Iwamoto, Kanagawa (JP); Yuhiro Sakakibara, Kanagawa (JP); Satoru Nakajima, Kanagawa (JP)

(73) Assignee: TANAKA KIKINZOKU KOGYO K.K., Tokyo (JP)

( * ) Notice: Subject to any disclaimer, the term of this patent is extended or adjusted under 35 U.S.C. 154(b) by 719 days.

(21) Appl. No.: 13/813,868

(22) PCT Filed: Aug. 3, 2011

(86) PCT No.: PCT/JP2011/067807
§ 371 (c)(1),
(2), (4) Date: Feb. 1, 2013

(87) PCT Pub. No.: WO2012/018057
PCT Pub. Date: Feb. 9, 2012

(65) Prior Publication Data
US 2013/0137192 A1 May 30, 2013

(30) Foreign Application Priority Data
Aug. 3, 2010 (JP) .................................. 2010-174930

(51) Int. Cl.
| | | |
|---|---|---|
| *G01N 33/553* | (2006.01) | |
| *G01N 33/538* | (2006.01) | |
| *G01N 33/543* | (2006.01) | |

(52) U.S. Cl.
CPC ..... *G01N 33/538* (2013.01); *G01N 33/54393* (2013.01); *G01N 33/553* (2013.01)

(58) Field of Classification Search
None
See application file for complete search history.

(56) References Cited

U.S. PATENT DOCUMENTS

| | | | | |
|---|---|---|---|---|
| 5,212,061 A | * | 5/1993 | Snyder ............. | G01N 33/56955 435/21 |
| 5,248,595 A | * | 9/1993 | Boyer .................. | G01N 33/531 435/7.32 |
| 5,641,635 A | * | 6/1997 | Emmons .............. | C12Q 1/6816 422/52 |
| 2003/0045003 A1 | | 3/2003 | Smith | |
| 2003/0143758 A1 | | 7/2003 | Shigenobu et al. | |
| 2008/0038772 A1 | * | 2/2008 | Filanoski ............. | C07D 501/00 435/40.5 |
| 2011/0129816 A1 | * | 6/2011 | Muraguchi ........ | C07K 16/1018 435/5 |
| 2011/0143457 A1 | * | 6/2011 | Minakawa ....... | G01N 33/54393 436/501 |
| 2011/0212485 A1 | * | 9/2011 | Mitragotri .............. | A61B 10/02 435/29 |

FOREIGN PATENT DOCUMENTS

| | | | | |
|---|---|---|---|---|
| JP | 2001-340099 | | 12/2001 | |
| WO | 02/003068 | | 1/2002 | |
| WO | 2009/110577 | | 9/2009 | |
| WO | 2009/148150 | | 12/2009 | |
| WO | 2010/007734 | | 1/2010 | |
| WO | WO 2010021399 A1 * | 2/2010 | ....... G01N 33/54393 |

OTHER PUBLICATIONS

Fu et al., "Chemical signal amplification in two-dimensional paper networks", Sensors and Actuators B: Chemical (2010) 149:325-328; Available online: Jun. 18, 2010.*
Chinese Office Action dated Apr. 28, 2014 for Chinese Patent Application No. 201180038036.3, and English translation.
Office Action dated May 2, 2014, in the corresponding European patent application Serial No. 11 814 682.8-1405.
Talon, R. et al., Prediction of *Streptococcus salivarius* subsp. *thermophilus* and *Lactobacillus delbrueckii* subsp. *bulgaricus* populations in yoghurt by Curie point pyrolysis-mass spectrometry, Journal of Microbiological Methods, 2002, vol. 48, No. 2-3, pp. 271-279.
Supplementary European Search Report dated Nov. 25, 2013 for EP Patent Application No. 11814682.8.
International Search Report for PCT/JP2011/067807, dated Nov. 1, 2011.

\* cited by examiner

*Primary Examiner* — Scott Long
*Assistant Examiner* — Gary E Hollinden
(74) *Attorney, Agent, or Firm* — Orrick, Herrington & Sutcliffe LLP; Joseph A. Calvaruso

(57) ABSTRACT

When an immunochromatography reagent composition containing a nonionic surfactant, an N,N-bis(2-hydroxyethyl) glycine buffer, and casein is used as a specimen treatment solution or developing solution in detecting a detection object in a specimen according to an immunochromatographic method, an immunochromatography reagent composition which suppresses a non-specific reaction; does not cause aggregation of antibody-immobilized colloidal gold; and has a high developing rate, in comparison with conventional technology which detects a detection object by using an immunochromatographic device; and a high-performance and highly-sensitivity immunochromatographic method and a detection kit capable of rapid, simple and easy virus detection, which use the immunochromatography reagent composition are provided.

5 Claims, No Drawings

IMMUNOCHROMATOGRAPHY REAGENT COMPRISING A NONIONIC SURFACTANT, BICINE, AND CASEIN, AND MEASUREMENT METHOD USING THE SAME

TECHNICAL FIELD

The present invention relates to a high-performance and high-sensitive reagent composition for immunochromatography which does not cause a non-specific reaction; a specimen treatment solution for immunochromatography; a developing solvent for immunochromatography; and a measurement method using the same.

BACKGROUND ART

In recent years, immunochromatographic strip type immunoassay has become increasingly important as a simple and easy in-vitro diagnostic kit or mobile diagnostic device for detecting an antigen in a sample solution by making use of the specific reactivity of an antibody. In particular, a pregnancy test kit is a familiar immunochromatographic device commercially available also as a non-prescription drug. Recently, simple and easy test tools based on the immunochromatographic method have been under development in order to determine the presence or absence of infection with a pathogen such as influenza virus or bacteria.

A test drug of the immunochromatographic method having an antibody labeled with an insoluble carrier has been used generally because it requires only a simple and easy operation and the test using it needs only a short time. However, in comparison with EIA, there has been a problem that it has generally low sensitivity and the line observed when the result is positive is not clear.

With a view to overcoming such a problem, a method of allowing sugar or a water-soluble high-molecular compound to exist in a developing solvent as in Patent Document 1 is proposed. However, even if this method is applied to the immunochromatographic method using an antibody labeled with an insoluble carrier, aggregation of the insoluble carrier may occur and a non-specific reaction may be caused. Problems such as low developing rate has not been able to be overcome (refer to Patent Document 1).

Therefore, there is an eager demand for the development of a test drug which does not cause aggregation of an insoluble carrier; does not cause a non-specific reaction; and has a high developing rate even if it is applied to the immunochromatographic method using an antibody labeled with an insoluble carrier.

For example, a method of easily analyzing a plurality of detection targets in a specimen by the membrane assay method using colored latex particles, wherein the colored latex particles have respectively different colors for two or more detection targets is proposed. The method is particularly effective for a detection object which is prone to false positive and more effective when two or more detection targets are selected from Influenza A virus, Influenza B virus, and RS virus (refer to Patent Document 2).

In a simple and easy testing method of a specimen by using the membrane assay method, a filtration method of a specimen sample capable of preventing a false positive result or clogging with keeping high sensitivity is provided (refer to Patent Document 3).

In Patent Documents 2 and 3, when the detection is conducted by the membrane assay method wherein a biological sample such as a swab from the nasal cavity or pharynx or an aspirate fluid from the nasal cavity is used, a suspension containing an MES buffer (Good's buffer), Triton X-100 (nonionic surfactant), protein such as bovine serum albumin or casein, and the like is used as a specimen suspension for suspending a specimen therein.

In Patent Document 4, in a testing method of respiratory infections by using a test tool based on the immunochromatographic method, a treatment solution containing a surfactant (NP40, or the like), a reducing agent (2-mercaptoethylamine hydrochloride, or the like), a thiocyanic acid compound, a chelating agent, a Good's buffers (PIPES, etc.), and the like is used as a specimen treatment solution for treating a specimen selected from a swab from the nasal cavity or pharynx and an aspirate fluid from the nasal cavity (Patent Document 4).

In the inventions described in Patent Documents 2 to 4, however, colored latex particles are used mainly as a labeling reagent and as a specimen treatment solution, conventionally employed ones are use since they do not take a particular attention to the specimen treatment solution.

Patent Document 5 takes an attention to a specimen treatment solution, which is used for the detection according to the membrane assay method. The treatment solution containing a nonionic surfactant (Nonion MN-811, or the like), bovine serum albumin, and a Tris-HCl buffer is used as a specimen treatment reagent composition to suppress a non-specific reaction (refer to Patent Document 5).

In Patent Document 6, as a specimen suspension composition, by using a treatment solution containing a nonionic surfactant (Triton X-100 or the like), a basic amino acid, a protein (bovine serum albumin, or the like) for stabilizing a substance to be measured, and a buffer (Tris-HCl, or the like) for keeping the pH at from 3 to 8, occurrence of a false positive result is prevented (refer to Patent Document 6).

However, the specimen treatment solution or developing solvent described in Patent Documents 2 to 6 has still the problem that it cannot fully suppress the aggregation of an insoluble carrier or induction of a non-specific reaction. Therefore, they are not fully satisfactory as a test drug having a high developing rate and there is an eager demand for further improvement.

PRIOR ART DOCUMENTS

Patent Documents

Patent Document 1: JP-A-2000-329767
Patent Document 2: JP-A-2008-014751
Patent Document 3: JP-A-2008-122372
Patent Document 4: JP-A-2008-164403
Patent Document 5: JP-A-2009-186359
Patent Document 6: JP-A-2006-084351

SUMMARY OF THE INVENTION

Problems to be Solved by the Invention

An object of the present invention is to provide a high-performance and high-sensitivity immunochromatography test drug which does not induce a non-specific reaction in comparison with the conventional technology by improving a specimen treatment solution or a developing solvent to be used in an immunochromatographic method test drug. In particular, an object is to improve a test treatment solution or developing solvent to be used in an immunochromatographic method test drug in order to provide a test drug causing no aggregation of antibody-immobilized colloidal gold and at the same time, having a high developing rate. Another object of the present invention is to provide an immunochromatographic device capable of speedily, easily, and precisely detecting an antigen (for example, viruses such as influenza virus, adenovirus, and RS virus) in a specimen (for example, a specimen collected from respiratory disease patients, particularly, nasal discharge, swab from the nasal cavity, or sputum) without causing a non-specific reaction compared with the conventional technology.

More specifically, an object is to provide a detection kit capable of testing a specimen speedily, easily, and highly precisely by adding dropwise of a detection sample treated with a specimen treatment solution or a developing solvent to a sample addition site of the detection kit to cause a specific reaction with an antigen in the specimen without causing a non-specific reaction.

Means for Solving the Problems

The present invention relates to an immunochromatography reagent composition, more specifically, a specimen treatment solution or a developing solvent to be used as an immunochromatographic method test drug when a specimen is tested by using an immunochromatographic device and it contains N,N-bis(2-hydroxyethyl)glycine (which is one of Good's buffers and will hereinafter be called "Bicine"), a nonionic surfactant, and casein.

The inventors of the present invention have found for the first time that a test drug which does not cause aggregation of an antibody-immobilized gold colloid and at the same time has a high developing rate can be provided by using an immunochromatography reagent composition containing Bicine, a nonionic surfactant, and casein as a specimen treatment solution or developing solvent to be used as an immunochromatographic method test drug.

In the detection system in the present invention, an immunochromatographic device capable of speedily, easily, and highly precisely detecting an antigen (for example, viruses such as influenza virus, adenovirus, and RS virus) in a specimen, for example, collected from respiratory disease patients (in particular, a nasal discharge, a swab from the nasal cavity, sputum, or the like) with suppressing a non-specific reaction by using an immunochromatography reagent composition containing Bicine, a nonionic surfactant, and casein is provided.

In addition, a detection kit capable of speedily, easily, and highly precisely carrying out a specimen test by adding dropwise of a specimen sample, which has been treated with a specimen treatment solution or developing solvent for immunochromatography containing Bicine, a nonionic surfactant, and casein, to a sample addition site of the detection kit, which causes a specific reaction with an antigen in the specimen with suppressing a non-specific reaction is further provided.

The present invention provides an immunochromatography reagent composition described below in from (a) to (h), a specimen treatment solution or an immunochromatography developing solution using thereof, an immunochromatographic device using thereof, a detection kit using thereof, and an immunochromatographic method using thereof.

(a) The first feature of the present invention is an immunochromatography reagent composition comprising a nonionic surfactant, an N,N-bis(2-hydroxyethyl)glycine buffer, and casein.

(b) The second feature of the present invention is the immunochromatography reagent composition according to (a), wherein the nonionic surfactant is polyoxyethylene (23) lauryl ether.

(c) The third feature of the present invention is the immunochromatography reagent composition according to (a) for use in a detection system using nanogold particles as a labeling substance.

(d) The fourth feature of the present invention is a specimen treatment solution for immunochromatography, comprising the immunochromatography reagent composition as described in any one of (a) to (c).

(e) The fifth feature of the present invention is the specimen treatment solution for immunochromatography according to (d), wherein the specimen is any of a nasal discharge, a swab from the nasal cavity or pharynx, or sputum.

(f) The sixth feature of the present invention is a detection kit comprising a specimen treatment solution for immunochromatography which contains a nonionic surfactant, an N,N-bis(2-hydroxyethyl)glycine buffer, and casein.

(g) The seventh feature of the present invention is a developing solution for immunochromatography to be used for detecting a detection object in a specimen, comprising a nonionic surfactant, an N,N-bis(2-hydroxyethyl)glycine buffer, and casein.

(h) The eighth feature of the present invention is an immunochromatographic method comprising using a developing solution for immunochromatography which contains a nonionic surfactant, an N,N-bis(2-hydroxyethyl)glycine buffer, and casein as a developing solution constituting a mobile phase.

EFFECTS OF THE INVENTION

The immunochromatography reagent composition according to the present invention contains Bicine, a nonionic surfactant, and casein. It is possible to provide a test drug which does not cause aggregation of antibody-immobilized colloidal gold and at the same time, having a high developing rate by using the immunochromatography reagent composition containing these three components as a specimen treatment solution or an immunochromatography developing solution.

In the detection system in the present invention, by using the immunochromatography reagent composition containing Bicine, a nonionic surfactant, and casein, an immunochromatographic device capable of speedily, easily, and precisely detecting an antigen (for example, viruses such as influenza virus, adenovirus, and RS virus), for example, in a specimen collected from respiratory disease patients (in particular, a nasal discharge, swab from the nasal cavity, sputum, or the like) without causing a non-specific reaction is provided. Although details of the principle of the suppressing mechanism have not been elucidated, aggregation between labeling substances which occurs via a highly viscous protein contained in the specimen such as nasal discharge or aggregation between a labeling substance and a chromatographic medium due to non-specific bonding is suppressed or a non-specific reaction does not occur between a labeling substance and a detection reagent on a chromatographic medium so that this device is free from deterioration in sensitivity by which the results can be judged correctly.

The detection kit of the present invention is advantageous since a detection sample treated with a specimen treatment solution for immunochromatography containing Bicine, a nonionic surfactant, and casein is added dropwise to a sample addition site of the detection kit and a specific reaction with an antigen in a specimen occurs without causing a non-specific reaction, a specimen test can be carried out speedily, easily, and highly precisely.

In addition, the present invention has the feature that a speedy, simple, and easy test can be carried out with using the developing solution for immunochromatography containing Bicine, a nonionic surfactant, and casein as a developing solution constituting a mobile phase.

BEST MODE FOR CARRYING OUT THE INVENTION

The present invention will hereinafter be described more specifically.

The embodiment of the present invention is based on an immunochromatographic method or a detection method using it, which is a method of forming a composite, by an antigen-antibody reaction on a chromatographic material, between a detection object (antigen) which is a substance to be detected in various specimens and a labeled substance (antibody) specifically binding thereto; developing it in the direction of an absorption site on the immunochromatographic medium; and confirming it by various detection means. As the antibody which most specifically reacts and binds with the antigen, for example, a monoclonal antibody, a polyclonal antibody, or another known antibody which specifically binds to the antigen can be used arbitrarily.

Although enzymes, chromogenic substances, fluorescent substances, or radioactive substances can be used arbitrarily as the label, the label may be determined in consideration of the characteristics of the immunochromatographic method, that is, easy operation and decreased detection time or in consideration of the kind of the antibody or antigen.

The detection means is characterized by that it enables correct judgment in visual judgment in order not to impair the characteristics of the immunochromatographic method, that is, easy operation and judgment in a relatively short period of time. When detection should be made in a limited time or precise detection is required, it is possible to carry out detection in combination with various detection means such as spectrophotometric detection and radiation detection.

It has been found as a result of study on a developing solution having a great influence on the accuracy of detection and a non-specific reaction in detecting using the immunochromatographic method that the following embodiment is most suited.

Namely, the inventors of the present invention have proceeded with an extensive investigations, in an immunochromatographic detection method using a developing solution containing a pH buffer and the like, on a substance effective for suppressing a side reaction due to biological affinity or for negating the hydrophobic bonding or electrical interaction, for example, surfactants, ammonium salts, pH buffers, and various additives for suppressing a non-specific reaction such as proteins for accelerating an antigen-antibody reaction or for suppressing a non-specific reaction. As a result, it has been found for the first time that by using an immunochromatography reagent composition containing Bicine, a nonionic surfactant, and casein, during detecting an antigen (for example, viruses such as influenza virus, adenovirus, and RS virus) in a specimen (particularly, nasal discharge, a swab from the nasal cavity, sputum, or the like) collected from, for example, respiratory disease patients, it is possible to suppress a side reaction due to biological affinity or a nonspecific reaction (noise) due to hydrophobic bonding and electrical interaction, although the suppressing mechanism has not been elucidated, while the antigen-antibody reaction was accelerated; a signal was increased; and no aggregation of an antibody-immobilized colloidal gold was increased. Thus the present invention was accomplished. In addition, when the reagent composition of the present invention is used for an immunochromatographic detection method, aggregation due to non-specific bonding between labeling substances or between a labeling substance and a chromatographic medium which occurs via a highly viscous protein contained in the specimen such as nasal discharge can be suppressed; a decrease in a developing rate due to clogging of the pore of the chromatographic material does not occur; and moreover, an increase in viscosity due to the highly viscous protein can be suppressed, which enables high-speed development without causing a deterioration in sensitivity and as a result and speedy detection.

Examples of the nonionic surfactant which can be incorporated in the immunochromatography reagent composition of the present invention include polyoxyethylene alkyl ethers, polyoxyethylene/polyoxypropylene alkyl ethers, polyoxyethylene sorbitan fatty acid esters ("Tween" series, trade name), polyoxyethylene p-t-octylphenyl ethers ("Triton" series, trade name), polyoxyethylene p-t-nonylphenyl ethers ("Triton N" series, trade name), alkyl polyglycosides, fatty acid diethanolamides, and alkyl monoglyceryl ethers. Of these, polyoxyethylene alkyl ethers are preferred. Polyoxyethylene (23) lauryl ether ("Brij 35"; trade name) and polyoxyethylene (20) cetyl ether ("Brij 58", trade name) are preferably used. Of these, polyoxyethylene (23) lauryl ether ("Brij 35"; trade name) is particularly preferred. The nonionic surfactant is desirably substantially free from a nonionic surfactant other than polyoxyethylene (23) lauryl ether ("Brij 35"; trade name). However, it is possible to mix another nonionic surfactant or an ionic surfactant without adversely affecting the present invention.

The content of the nonionic surfactant to be incorporated in the immunochromatography reagent composition of the present invention is within a range of from 0.01 to 10 weight %, preferably from 0.05 to 5 weight % based on the total weight of the immunochromatography reagent composition. The content less than 0.01 weight %, for example, 0.005 weight %, is insufficient for conducting a correct judgment. When the content is less than 0.05 weight %, it tends to become difficult to conduct a correct judgment because a non-specific reaction cannot be repressed. When the content is 10 weight % or greater, for example, 12 weight % or 18 weight %, the concentration of the nonionic surfactant exceeds a required one and it not only has an undesirable influence on the control of a nonspecific reaction but also becomes technologically meaningless. Such an amount is not economical but is wasteful.

Typical examples of a salt to be incorporated in the immunochromatography reagent composition such as extraction and developing solution in the present invention include sodium chloride, potassium chloride, calcium chloride, and magnesium chloride. Sodium chloride is preferred.

The concentration of the salt to be incorporated in the immunochromatography reagent composition such as extraction and developing solution in the present invention falls within a range of from 1 mM to 500 mM; preferably from 5 mM to 200 mM; more preferably from 10 mM to 50 mM with respect to the whole immunochromatography reagent composition. The concentration less than 1 mM, for example, 0.1 mM is not sufficiently effective for the protein extraction. The concentration of 500 mM or greater, for example, 1 M or 2 M is technologically meaningless. The concentration thus exceeding a required concentration is not economical but wasteful.

The salts to be incorporated in the immunochromatography reagent composition in the present invention may be used either singly or in combination of two or more.

The concentration of the Bicine buffer, one of the components of the immunochromatography reagent composition in the present invention, is within a range of preferably from 10 to 200 mM; more preferably from 10 to 100 mM; still more preferably from 30 to 100 mM with respect to the entire immunochromatography reagent composition. The Bicine buffer having a concentration less than 10 mM cannot have a sufficient buffer effect and in addition, cannot suppress aggregation of labeling particles sufficiently. When the concentration is 200 mM or greater, it exceeds a required concentration and is therefore not economical but wasteful. It is most suited to prepare it as a buffer having a pH range from 7.7 to 9.1.

The immunochromatography reagent composition of the present invention is preferably substantially free from a buffer other than Bicine. However, another buffer may be mixed insofar as it does not adversely affecting the present invention.

As the casein, one of the components of the immunochromatography reagent composition of the present invention, it is preferred to use casein alone but a reagent containing casein, for example, powdered skim milk may be used. The concentration of casein falls within a range of preferably from 0.01 to 20 weight %; more preferably from 0.1 to 10 weight %; and still more preferably from 0.5 to 5 weight % based on the total weight of the immunochromatography reagent composition. The amount less than 0.01 weight % is insufficient for correct judgment because it cannot suppress a non-specific reaction. The amount of 20 weight % or greater is above the necessary concentration and it is not economical but wasteful.

It is possible and effective to incorporate, in the immunochromatography reagent composition of the present invention, one or two kinds of additives known to suppress a side reaction due to biological affinity or suppress a nonspecific reaction, for example, proteins for accelerating an antigen antibody reaction or suppressing a non-specific reaction (such as bovine serum albumin, gelatin etc.), high molecular compounds (such as polyethylene glycol, methyl cellulose, polyvinylpyrrolidone, polyvinyl alcohol, dextran etc.), and ionic surfactants or polyanions (such as dextran sulfuric acid, heparin, polystyrene sulfonic acid, chondroitin sulfuric acid etc.). Incorporation of them does not interfere with the effects of the present invention. It is also possible and effective to retain, on a transfer pathway of a mobile phase on a chromatographic medium constituting a stationary phase, one or more of proteins, high molecular compounds, ionic surfactants or polyanions, or antibiotics for accelerating an antigen antibody reaction or repressing a non-specific reaction. Retention of them does not interfere with the effects of the present invention.

The immunochromatography reagent composition of the present invention can be used most suitably as a developing solution. It can also be used suitably as a treatment solution of a specimen sample. The using method of the composition is not limited to the above one, but can also be used by providing the components of the immunochromatography reagent composition on a transfer pathway of a mobile phase on the immunochromatographic medium. As the developing solution, water is typically used as a solvent and the Bicine buffer, casein, and the nonionic surfactant are added to it. The adding order is not particularly limited and they may be added simultaneously. When the composition is used as a developing solution, development can be conducted by supplying/adding dropwise of a mixture of a sample to be detected (specimen sample) and the developing solution obtained in advance on a sample pad (sample addition portion) or supplying/adding dropwise of the sample on a sample pad (sample addition portion) in advance and then supplying/adding dropwise of the developing solution on the sample pad (sample addition portion). When the composition is used as a specimen treatment solution, the specimen sample is diluted in advance with the treatment solution and then, the resulting treatment solution is supplied/added dropwise on a sample pad (sample addition portion) as is as the developing solution.

When the component of the immunochromatography reagent composition of the present invention is used by providing it on a transfer pathway of a mobile phase on an immunochromatographic medium, it can be achieved, for example, by a method of applying the composition on a sample pad (sample addition portion) in an immunochromatographic device or impregnating the sample pad with it and then drying to support or retain it in the sample pad. In another mode, the immunochromatography reagent composition of the present invention is retained or supported on an immunochromatographic medium by providing an additive retaining portion at a desired site between the end of the sample addition portion and an absorption portion and retain the composition on the additive retaining portion. The additive retaining portion may be, for example, the sample addition portion or a labeling substance retention portion, or on the immunochromatographic medium. Above all, the composition can be supported or retained only on the sample addition portion and/or labeling substance retention portion.

The sample (specimen) containing the detection object of the present invention is, for example, mainly a biological sample and specific examples include blood, serum, plasma, urea, saliva, spinal fluid, sweat, tear, amniotic fluid, discharge from the nipple, nasal discharge, sputum, swab from the nasal cavity or pharynx, skin exudate, and extract from the tissue, cell, or feces.

There is no particular limitation is in the detection object in the present invention insofar as there is a substance specifically binding to it, for example, a substance specifically binding as in an antigen antibody reaction or such a substance can be prepared. The detection object may be a complete antigen which itself has antigenicity or may be a hapten (incomplete antigen) which itself has no antigenicity but can have antigenicity by the chemical modification. In short, it is only necessary that a substance specifically binding to the detection object exists or can be prepared. It may be a monoclonal antibody or a polyclonal antibody. Examples of the detection object in the present invention include peptide hormones (growth hormone (GH), adrenocorticotropic hormone (ACTH), melanocyte stimulating hormone (MSH), prolactin, thyroid stimulating hormone (TSH), luteinizing hormone (LH), follicle stimulating hormone (FSH), hypophyseal hormone, calcium metabolism regulating hormone, renal hormone, gut hormone, vasoactive hormone, and placental hormone such as human chorionic gonadotropic hormone (hCG)), prostatic acid phosphatase (PAP), prostate specific antigen (PSA), alkali phosphatase, transaminase, trypsin, pepsinogen, α-fetoprotein (AFP), tumor specific substances such as carcinoembryonic antigen (CEA), serum protein components such as immunoglobulin G (IgG), rheumatism factors, serotonin, Urokinase, ferritin, substance P, estrogens such as estrone, fecal occult blood, syphilitic antibody, influenza virus, adenovirus, RS virus, rotavirus, HBs antigen, HBs antibody, chlamydial antigen, bacterial antigens such as *Streptococcus pyogens* antigen, natural or synthetic progestational hormone, androgens such as testosterone, adrenocortical hormones such as cortisol, other steroids such as cholesterol, bile acid, cardiotonic steroid, and sapogenin, epinephrine, dopamine, physiologically active alkaloids, amino-containing psychotropic agents, low molecular weight peptides such as TRH, thyroid hormones such as diiodothyronine, prostaglandins, vitamins, antibiotics such as penicillin, other in-vivo components, and drugs to be administered in vivo and metabolites thereof. Of these detection objects, viruses are preferred and influenza virus, adenovirus, and RS virus are more preferred.

The specimen most suited in the present invention is nasal discharge, a swab from the nasal cavity or pharynx, or sputum. By diluting such a specimen with the specimen treatment solution of the present invention in advance, an antigen (virus: mainly, influenza virus, adenovirus, RS virus) collected from respiratory disease patients can be detected exactly as a detection target.

The structure and operation and detection method of an immunochromatographic device for detecting a detection target in a specimen are known (refer to, for example, Patent Document 5).

Tests such as identification and quantification of a detection target in a specimen can be conducted by adding dropwise of a specimen sample, which has been obtained in advance by diluting the specimen with the specimen treatment solution of the present invention, into a sample pad of a conventional immunochromatographic device and developing the specimen sample in the direction of an absorption site on the immunochromatographic medium to cause an antigen antibody reaction.

The immunochromatographic device will hereinafter be described.

Conventionally, an immunochromatographic device is comprised of (1) a sample addition site (which is also called "sample pad"), (2) a labeled substance retention site, (3) a chromatographic medium, (4) a detection site (which is also called "judgment portion"), (5) an absorption site, and (6) a packing sheet.

The sample addition site (1) is made of a porous sheet such as glass filter paper which permits rapid absorption of a sample but has a weak retention power so that it enables prompt transfer of the sample to a reaction site.

Moreover, if necessary, in order to suppress a non-specific reaction more effectively, it is also possible to apply the immunochromatography reagent composition of the present invention containing three components: Bicine, casein, and a nonionic surfactant to the sample pad (1) or to any region between the end of the sample pad (1) and the absorption portion (5) or impregnate the sample pad or the above region with the composition in advance followed by drying by which the composition is retained or hold thereon.

The labeled substance retention site (2) retains a labeled reagent obtained by labeling a reagent component with a labeling component. Examples of the labeling component include colloidal metal particles, latex particles, enzymes, and fluorescent compounds. Of these, colloidal metal particles are most suited. The reagent component is a particle or a molecule having an ability of recognizing an analyte, preferably a monoclonal antibody or a polyclonal antibody, or a fragment thereof (second reagent).

As the colloidal metal particles, single particles or composite particles of a noble metal such as silver, platinum, germanium, rhodium or palladium are preferably used arbitrarily. In particular, since gold is sensitive to a change in hue, it is most suited. Judging from the state of colloidal metal particles, the average particle size is from about 1 to 500 nm; preferably from about 10 to 250 nm; more preferably from about 35 to 100 nm. It is contained in an amount of from about 0.0001 to 0.08 weight %, preferably from about 0.002 to 0.06 weight % based on the medium. The term "nanogold particles" as used herein means various colloidal gold particles having such a nano-sized average diameter. In immunological measurement, colloidal gold composite particles, which have been obtained by retaining colloidal platinum particles on the surface of colloidal gold particles with consideration of the particle diameter, particle size distribution, and color tone of the colloidal gold, can be used as a label for immunological measurement and can be used for enhancing the usefulness as a dye of proteins. Moreover, measurement sensitivity can be enhanced by using a so-called sensitizer such as colloidal gold label amplifier having a functional group capable of binding to the surface of metal particles and a reaction group capable of binding to an antibody. Nano colloids of these noble metals can be prepared in a conventional manner, for example, by adding a known reducing agent to an aqueous solution of a chloride of a noble metal acid, nitric acid noble metal acid, or nitric acid noble metal acid. They can be measured by various conventional methods such as determination of an average particle size after measurement of the particle size distribution of colloids by using a dynamic light scattering particle size analyzer.

As the colloidal metal particles to be used in the present invention, various commercially available colloidal metal particles and colloidal metal particle suspension can be used. For example, a colloidal gold suspension ("LC40 nm", product of Tanaka Precious Metals) can be used.

The chromatographic medium (3) has the detection site (4) on a membrane carrier. There is no particular limitation in the membrane carrier insofar as it can absorb and transfer a sample specimen through capillary action. For example, it can be selected from the group consisting of nitrocellulose, cellulose acetate, nylon, polyether sulfone, polyvinyl alcohol, polyesters, glass fibers, polyolefins, and cellulose, and artificial polymers made of mixed fibers thereof.

At the detection site (4), a monoclonal antibody or a polyclonal antibody, or a fragment thereof (first reagent) is supported and fixed on a nitrocellulose sheet.

The absorption site (5) is made of a material having the ability to rapidly absorb an excess sample, for example, glass filter paper.

The packing sheet (6) is a base material. By applying or attaching an adhesive or an adhesive tape to one side of the sheet, respectively, the sheet has adhesiveness on one side and some or all of the sample addition site (1), labeled substance retention site (2), chromatographic medium (3), detection site (4), and absorption site (5) are bonded firmly on the tacky surface of the sheet. The packing sheet (6) is not particularly limited as a base material insofar as it is made impermeable or moisture impermeable to the sample solution by the pressure-sensitive adhesive.

Either one or both of the reagent component (first reagent) to be used for the detection site (4) and the reagent component (second reagent) to be used for the labeling reagent may be a monoclonal antibody or a polyclonal antibody. The reagent component (second reagent) to be used for the labeling reagent is preferably a monoclonal antibody having high specificity from the standpoint of measurement sensitivity or the like. The reagent component (first reagent) to be used for the detection site (4) may be either a monoclonal antibody or a polyclonal antibody.

The monoclonal antibody or polyclonal antibody, or a fragment thereof is known and is available. It can be prepared in a known manner. Examples of antibody producing animals include human, mouse, rat, rabbit, and goat. As an immunoglobulin, any of IgG, IgM, IgA, IgE, and IgD may be used.

The monoclonal antibody can be obtained by the conventional method. Splenic cells and myeloma cells of mice immunized with an antigen (for example, influenza A virus) are hybridized. A hybridoma that produces a target antibody is selected and a monoclonal antibody produced therefrom is obtained. Refer to, for example, the method announced by Köhler and Milstein (Nature, 256 (1975), 495-497).

The polyclonal antibody can be obtained in a usual manner by isolating a target antibody from an anti-serum obtained by immunizing a producing animal (such as human, mouse, rat, rabbit, goat, or horse) with an antigen (for example, influenza A virus).

Although it is described in Examples of the present invention that a mouse-derived anti-influenza A monoclonal antibody is used as the reagent component (second reagent) to be used for the labeling reagent and a mouse-derived anti-influenza A monoclonal antibody is used as the reagent component (first reagent) to be used for the detection site (4), the reagent components are not limited to them. A mouse-derived anti-influenza A polyclonal antibody can also be used.

The following is the outline of a judgment principle.

1. A predetermined amount (usually from 0.1 to 2 ml) of a specimen sample (specimen diluted with the specimen treatment solution) is added by dropwise on the sample pad (1). When the specimen sample is added by dropwise, although it is absorbed quickly in the sample pad (1), the resulting pad starts moving immediately together with the sample. When the sample pad (1) is impregnated with the immunochromatography reagent composition, the immunochromatography reagent composition is dissolved in the water content of the specimen sample and starts moving together with the specimen sample.

2. The specimen sample first moves to the labeled substance retention site (2). When the specimen sample passes through this site, the labeling reagent (second reagent) retained on the labeled substance retention site (2) is dissolved in the water content of the sample and moves together with the sample.

3. Next, the labeling reagent dissolved in the water content of the specimen sample passes through the detection site (4) on the chromatographic medium (3). Here, a non-specific binding reaction is suppressed by the immunochromatography reagent composition dissolved in the specimen sample. When the specimen sample contains a detection target (for example, antigen), it specifically reacts with and binds to the antibody supported and fixed on the detection site (4) so as to be sandwiched between the antibody and the labeling reagent due to the antigen-antibody specific binding reaction, by which the detection site (4) is colored. When the specimen sample does not contain a detection target (for example, antigen), the labeling reagent dissolved in the water content of the sample, even if the sample passes through the detection site (4) on the chromatographic medium (3), a specific binding reaction does not occur. Therefore, the detection site (4) is not colored.

4. Lastly, the water content of the sample moves to the absorption site (5).

Thus, the presence or absence of a detection target (for example, an antigen) in the specimen sample can be exactly judged.

EXAMPLES

Although the effectiveness of the present invention will hereinafter be described by Examples, the present invention is not limited to or by them. In the present invention, unless otherwise specified, a ratio, part or parts, %, and the like are calculated on a weight basis.

Example 1=Brij 35

(1) Preparation of Judgment Portion on a Chromatographic Medium

As a membrane, a sheet ("HF 120", trade name; product of Millipore, 300 mm×25 mm) made of nitrocellulose was used. A mouse-derived anti-influenza A monoclonal antibody (first antibody) was diluted with a phosphate buffer (pH 7.4) containing 5 weight % isopropyl alcohol to give the concentration of 1.0 mg/ml. The resulting solution (150 µL) was applied on the membrane with the width of 1 mm, followed by drying at 50° C. for 30 minutes and then drying overnight at room temperature to prepare a chromatographic medium.

(2) Preparation of a Labeling Substance Solution

To 0.5 ml of a colloidal gold suspension ("LC40 nm", product of Tanaka Kikinzoku Kogyo) 0.1 ml of a mouse-derived anti-influenza A monoclonal antibody (second antibody) diluted with a phosphate buffer (pH 7.4) was added to give the concentration of 0.05 mg/ml followed by allowing to stand at room temperature for 10 minutes. Then, 0.1 ml of a phosphate buffer (pH 7.4) containing 1 weight % bovine serum albumin (BSA) was added, followed by allowing to stand at room temperature for 10 minutes. After thorough stirring, centrifugation was carried out for 15 minutes at 8000×g. After removal of the supernatant, 0.1 ml of a phosphate buffer (pH 7.4) containing 1 weight % BSA was added. A labeling substance solution was prepared in the above-mentioned manner.

(3) Preparation of Immunochromatography Test Piece

After addition of a mixture, which had been obtained by adding 300 µL of a 10 weight % aqueous trehalose solution and 1.8 mL of distilled water to 300 µL of the labeling substance solution prepared above, to a 15 mm×300 mm glass fiber pad (product of Millipore) uniformly, drying in a vacuum drier was carried out to prepare a labeling substance retention member. Next, the chromatographic medium prepared above, the labeling substance retention member, a sample pad (product of Millipore: 300 mm×30 mm) to be used as a portion to which a sample is added, and an absorption pad for absorbing the developed sample or labeling substance were bonded to a base material made of a packing sheet. The resulting laminate was cut into a 5-mm wide piece by a cutter and the piece was used as an immunochromatography test piece.

(4) Preparation of a Specimen Treatment Reagent

A 50 mM Bicine buffer (pH 8.5) containing 2 weight % casein, 25 mM KCl, 1 weight % Brij 35 (product of Takara Bio Inc.), and 0.095% sodium azide was prepared and the resulting buffer was used as a reagent for treating a specimen such as nasal discharge, sputum, or a swab from the nasal cavity.

(5) Judgment

The presence or absence of influenza A virus in a sample was measured according to the following method by using the immunochromatography test piece prepared above.

Specifically, a nasal discharge was collected by inserting one end of the tube of a suction trap in a suction pump and the other end of the tube in the inner part of the nasal cavity of a person who is not suffered from influenza and setting the suction pump at negative pressure. The nasal discharge thus collected was diluted to 20 times with the specimen treatment reagent to obtain a negative specimen sample. A positive specimen sample was obtained by adding a commercially-available inactivated influenza A virus to the negative specimen sample so as to give the protein concentration of 25 ng/mL or 50 ng/mL. The negative specimen sample and the positive specimen sample, each 150 mL, were placed and developed on the sample pad of the immunochromatography test piece and 15 minutes later, visual judgment was conducted. When a red test line was confirmed, the sample was judged as "+"; when a red line was confirmed but it was a very pale red line, the sample was judged as "±"; and when no red line was confirmed, the sample was judged as "−". The results are shown in Table 1.

Example 2=Tween 20

In a manner similar to that of Example 1 except for the use of polyoxyethylene (20)-sorbitan monolauric acid ester (Tween 20, trade name) instead of Brij 35, the measurement was conducted. The results are shown in Table 1.

Example 3=Triton X-100

In a manner similar to that of Example 1 except for the use of polyoxyethylene (10)-p-t-octylphenyl ether (Triton X-100; trade name) instead of Brij 35, the measurement was conducted. The results are shown in Table 1.

Comparative Example 1=Tricine

In a manner similar to that of Example 1 except for the use of Tricine (pH 8.5) which is a secondary amine instead of Bicine, the measurement was conducted. The results are shown in Table 1.

Comparative Example 2=BES

In a manner similar to that of Example 1 except for the use of 2-{N,N-bis(2-hydroxyethyl)}aminoethanesulfonic acid (one of Good's buffers, which will hereinafter be abbreviated as "BES") (pH 8.0) which is a tertiary amine instead of Bicine, the measurement was conducted. The results are shown in Table 1.

Comparative Example 3=BSA

In a manner similar to that of Example 1 except for the use of BSA instead of casein, the measurement was conducted. The results are shown in Table 1.

Comparative Example 4=Without Brij35

In a manner similar to that of Example 1 except for the omission of Brij 35, the measurement was conducted. The results are shown in Table 1.

TABLE 1

| | 0 ng/mL | 25 ng/mL | 50 ng/mL | Aggregation of labeling particles | Time until a control line can be recognized (min) |
|---|---|---|---|---|---|
| Example 1 | − | + | + | None | 1 |
| Example 2 | − | ± | + | None | 1.2 |
| Example 3 | − | ± | + | None | 1.2 |
| Comparative Example 1 | − | ± | + | Present | 1.2 |
| Comparative Example 2 | − | − | ± | Present | 1.8 |
| Comparative Example 3 | + | + | + | Present | 1.2 |
| Comparative Example 4 | + | + | + | Present | 2.7 |

As described above, in Examples 1 to 3, a developing solution causing neither aggregation of antibody-sensitized colloidal gold nor non-specific reaction and having a high developing rate was realized by using the specimen treatment reagent composition containing Bicine, casein, and a nonionic surfactant (Brij35, Tween 20, or Triton X-100).

When the measurement was conducted in a manner similar to Example 1 except for the use of Tricine instead of Bicine as a buffer (Comparative Example 1), a red line was recognized but the color of it was very pale in the positive specimen sample having a 25 ng/mL concentration. In addition, since aggregation of the antibody-sensitized colloidal gold occurred, it was not satisfactory as a test kit.

When the measurement was conducted in a manner similar to Example 1 except for the use of BES instead of Bicine (Comparative Example 2), a red line was not recognized in the positive specimen sample having a concentration of 25 ng/mL. In the positive specimen sample having a 50 ng/mL concentration, although a red line was recognized, the color was very pale. In addition, aggregation of the antibody-sensitized colloidal gold occurred and the developing rate was low, which prevented exact judgment so that this sample was not desired as a detection kit.

When the measurement was conducted in a manner similar to Example 1 except for the use of BSA instead of casein (Comparative Example 3), a non-specific reaction with the negative specimen sample occurred and in addition, aggregation of the antibody-sensitized colloidal cold occurred, which prevented exact judgment.

When the measurement was conducted in a manner similar to Example 1 except for the omission of Brij 35 (Comparative Example 4), a non-specific reaction with the negative specimen sample occurred. In addition, aggregation of the antibody-sensitized colloidal cold occurred and the developing rate was slow, which prevented exact judgment.

These results have revealed that in measurement using the immunochromatographic method, it is possible to make exact judgment at a high developing rate without causing aggregation of antibody-sensitized colloidal gold, thus producing marked effects by using, as a specimen treatment solution, a reagent composition containing three components: Bicine as a buffer, casein as a protein accelerating an antigen antibody reaction and suppressing a non-specific reaction, and a nonionic surfactant.

Next, specimen treatment solutions containing various concentrations of Bicine were prepared and influenza virus was detected and measured (Examples 4 and 5). The measurement was conducted in a manner similar to Example 1 except that the concentration of Bicine used for the preparation of the specimen treatment reagent was changed. The results are shown in Table 2.

TABLE 2

| | Bicine concentration (mM) | 0 ng/mL | 25 ng/mL | 50 ng/mL | Aggregation of labeling particles | Time until a control line was confirmed (min) |
|---|---|---|---|---|---|---|
| Example 4 | 20 | − | + | + | None | 1.2 |
| Eample 5 | 100 | − | + | + | None | 1 |

It has been confirmed from the above-mentioned results that even if the concentration of Bicine was changed to 200 mM and 100 mM in Example 4 and 5, respectively, neither aggregation of antibody-sensitized colloidal gold nor nonspecific reaction occurred and in addition, they have a high developing rate which is similar with Example 1.

INDUSTRIAL APPLICABILITY

When the developing solvent or specimen treatment solution of the present invention is used in the immunochromatographic method which uses nanogold particles as a labeling substance and detects a detection target by making use of an antigen antibody reaction, there is a superior advantage that aggregation of antibody-sensitized colloidal gold does not occur and a developing speed is high. Due to such excellent advantages, it enables a high-sensitivity and rapid clinical test so that it has high industrial applicability.

The present invention is described in detail or with referring to some specific embodiments. It is apparent for those skilled in the art that various changes or modifications can be given without departing from the spirit and scope of the present invention.

The present application is based on Japanese Patent Application (Japanese Patent Application No. 2010-174930) filed on Aug. 3, 2010 and the content of which is incorporated herein by reference. All the references cited are incorporated herein as a whole.

The invention claimed is:

1. An immunochromatographic detection system comprising:
    an immunochromatography reagent composition that makes contact with a specimen,
    wherein the immunochromatography reagent composition comprises a nonionic surfactant from 0.01 to 10 weight %, an N,N-bis(2-hydroxyethyl)glycine buffer from 10 to 200 mM, and casein from 0.01 to 20 weight %; a chromatographic medium; and
    a labelling substance.

2. The immunochromatographic detection system according to claim 1, wherein the nonionic surfactant of the immunochromatography reagent composition is polyoxyethylene (23) lauryl ether.

3. The immunochromatographic detection system according to claim 1, wherein the labeling substance comprises nanogold particles.

4. An immunochromatographic detection kit comprising:
    a specimen treatment solution for immunochromatography which contains a nonionic surfactant, from 0.01 to 10 weight %, an N,N-bis(2-hydroxyethyl)glycine buffer from 10to 200 mM, and casein from 0.01 to 20 weight %; and
    a chromatographic medium.

5. An immunochromatographic method comprising:
    applying a developing solution to a sample pad of an immunochromatographic device,
    wherein the developing solution comprises a nonionic surfactant from 0.01 to 10 weight %, an N,N-bis(2-hydroxyethyl)glycine buffer, from 0.01 to 200 mM, and casein from 0.01 to 20 weight %; and
    applying a specimen sample to the sample pad.

* * * * *

UNITED STATES PATENT AND TRADEMARK OFFICE
CERTIFICATE OF CORRECTION

PATENT NO.         : 9,952,207 B2
APPLICATION NO.    : 13/813868
DATED              : April 24, 2018
INVENTOR(S)        : Yuhiro Sakakibara, Hisahiko Iwamoto and Satoru Nakajima Page 1 of 1

It is certified that error appears in the above-identified patent and that said Letters Patent is hereby corrected as shown below:

In the Claims

Claim 5, Column 16, Line 36, change "glycine buffer, from 0.01 to 200 mM" to -- glycine buffer from 10 to 200 mM --.

Signed and Sealed this
Third Day of July, 2018

Andrei Iancu
*Director of the United States Patent and Trademark Office*